(12) United States Patent
Kjeldsen et al.

(10) Patent No.: US 6,358,705 B1
(45) Date of Patent: Mar. 19, 2002

(54) METHOD OF MAKING PROTEINS IN TRANSFORMED YEAST CELLS

(75) Inventors: Thomas Kjeldsen, Virum; Knud Vad, Vanløs, both of (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/347,782

(22) Filed: Jul. 6, 1999

Related U.S. Application Data

(60) Provisional application No. 60/097,605, filed on Aug. 24, 1998.

(30) Foreign Application Priority Data

Jul. 16, 1998 (DK) .......................................... 1998 00945
May 28, 1999 (DK) .......................................... 1999 00754

(51) Int. Cl.⁷ .......................... C12P 21/02; C12N 15/64; C12N 15/74
(52) U.S. Cl. .................... 435/69.1; 435/91.42; 435/483
(58) Field of Search .............................. 435/69.1, 91.42, 435/483

(56) References Cited

FOREIGN PATENT DOCUMENTS

| | | |
|---|---|---|
| EP | 0 241 435 A2 | 10/1987 |
| EP | 0 251 579 A2 | 1/1988 |
| EP | 0 284 044 A1 | 9/1988 |
| EP | 0 286 424 A1 | 10/1988 |
| EP | 0 406 003 A1 | 1/1991 |
| EP | 0 438 200 A1 | 7/1991 |
| EP | 0 501 914 A1 | 9/1992 |
| EP | 0 592 358 A2 | 4/1994 |
| EP | 0 635 574 A1 | 1/1995 |
| EP | 0 674 006 A1 | 9/1995 |
| EP | 0 814 165 A2 | 12/1997 |
| WO | WO 94/00554 | 1/1994 |

*Primary Examiner*—Terry McKelvey
(74) *Attorney, Agent, or Firm*—Reza Green, Esq.

(57) ABSTRACT

The present invention relates to a method for expressing heterologous proteins or polypeptides in yeast by culturing a transformed yeast strain which does not contain a functional antibiotic resistance marker gene.

7 Claims, 6 Drawing Sheets

METHOD OF MAKING PROTEINS IN TRANSFORMED YEAST CELLS

This application claims priority under 35 U.S.C. §119 of U.S. provisional application Ser. No. 60/097,605 filed on Aug. 24, 1998, the contents of which are fully incorporated herein by reference. The application also claims priority under 35 U.S.C. §119 of Danish applications serial nos. PA 1998 00945 filed Jul. 16, 1998 and PA 1999 00754 filed on May 28, 1999.

FIELD OF INVENTION

The present invention relates to expression of proteins in transformed yeast cells, DNA construct and vectors for use in such process and yeast cells transformed with the vectors.

BACKGROUND OF THE INVENTION

It is well known to use transformed yeast strains for the expression of proteins see for example European patent applications Nos. 0088632A, 0116201A, 0123294A, 0123544A, 0163529A, 0123289A, 0100561A, 0189998A and 0195986A, PCT patent applications Nos. WO 95/01421, 95/02059 and WO 90/10075, and U.S. Pat. No. 4,546,082.

It is a common feature of the above methods that the yeast production plasmid contains a gene for an antibiotic marker. Such marker gene stems from the initial cloning steps in *E. coli* where it was used to screen for transformed cells or to maintain plasmids used as vectors. The antibiotic marker genes are not believed to have any adverse impact on the culturing of the transformed yeast cell and it has therefore been common practice not to take any steps to delete such DNA. In addition, characterization of the plasmid construct is usually done by isolation of plasmids from the transformed yeast cells and transformation of the isolated plasmid into *E. coli* followed by antibiotic selection. It has thus been convenient for practical purposes to retain the antibiotic resistance marker gene.

Although both research laboratories and industrial production plants are controlled by very severe safety regulations there is always a small risk that a few cells by accident will be released to the environment. Due to their highly sophisticated nature such genetically engineered microorganisms will only survive for a very short period and the risk of harming the environment is extremely low. This is of course the reason why such transformed microorganisms have been approved for use in both research and in large scale operations.

Even if the cells die quickly the plasmids containing the antibiotic resistant gene may still accidentally be disposed to the environment and there is a theoretical risk of introduction of resistance to antibiotics in bacteria if the plasmid is taken up spontaneously.

Antibiotics are of great importance for treatment of human and animal bacterial infections. Any risk of a potential environmental contamination with a gene that confers resistance to antibiotics should be minimized, if possible.

There is therefore a need to develop even more safer methods than the methods used up to this day and it is the object of the present invention to provide such improved methods.

SUMMARY OF THE INVENTION

The present invention relates to a method for expressing heterologous proteins or polypeptides in yeast wherein the yeast transformant strain used for production contains an expression vector in which an antibiotic marker gene used in the initial cloning steps has been made non functional by in vitro modification before transformation of the yeast host. The present invention also relates to DNA sequences and expression vectors for use in such method and to transformed yeast cells.

According to one aspect the present invention is related to a recombinant yeast expression vector being unable to confer antibiotic resistance to bacteria cells and comprising a gene coding for a heterologous gene and an antibiotic resistance marker gene which has been made non functional by in vitro modification.

According to a further aspect the present invention is related to a method for making a desired polypeptide or protein said method comprises culturing a yeast strain comprising a vector being unable to confer antibiotic resistance to bacteria cells and comprising a gene coding for a heterologous gene and an antibiotic resistance marker gene, which marker gene has been made non functional by in vitro modification before transformation of the yeast host, and isolating the desired product from the culture medium.

The method according to the invention will typically comprise culturing a yeast strain containing a yeast expression plasmid in which plasmid a functional antibiotic marker gene used for initial cloning steps in bacteria has been made non-functional by in vitro deletion of part of the marker gene or the whole marker gene before insertion into the yeast host to be used for expression and secretion of the desired polypeptide or protein.

The deletion of the antibiotic marker gene is preferably made by insertion of suitable restriction cleavage sites on each side of the antibiotic resistance marker gene whereupon the marker gene is deleted by in vitro treatment with suitable restriction enzymes.

The present invention is also related to transformed yeast strains comprising a vector being unable to confer antibiotic resistance to bacteria cells and comprising a gene coding for a heterologous gene and an antibiotic resistance marker gene which has been made non functional by in vitro modification before transformation of the yeast host.

The yeast strain is preferable a Saccharomyces strain, and in particular a *Saccharomyces cerevisiae* strain.

As used herein the expression "antibiotic marker gene" or "antibiotic resistance marker gene" means a gene that allows phenotypic selection of transformed bacterial cells and plasmid amplification.

The most commonly used antibiotic resistance marker genes in *E. coli* are the ampicillin (AMP), chloramphenicol, neomycin, kanamycin and tetracylin resistance conferring marker genes.

As used herein the expression "non functional marker gene" means that the marker gene has been either deleted or made non functional by deletion of part of the gene. It is preferred that the gene is completely deleted.

As used herein "in vitro modification" means modification steps performed on the vector outside the cell environment.

As used herein "unable to confer antibiotic resistance to bacteria cells" means that the antibiotic resistance genes are non functional in any organism due to the described gene manipulation.

As used herein the "yeast host" means a yeast organism to be transformed or transfected with the expression plasmid or vector.

BRIEF DESCRIPTION OF THE DRAWINGS

The present invention is further illustrated with reference to the appended drawings, wherein.

DETAILED DESCRIPTION OF THE INVENTION

Figure 1:
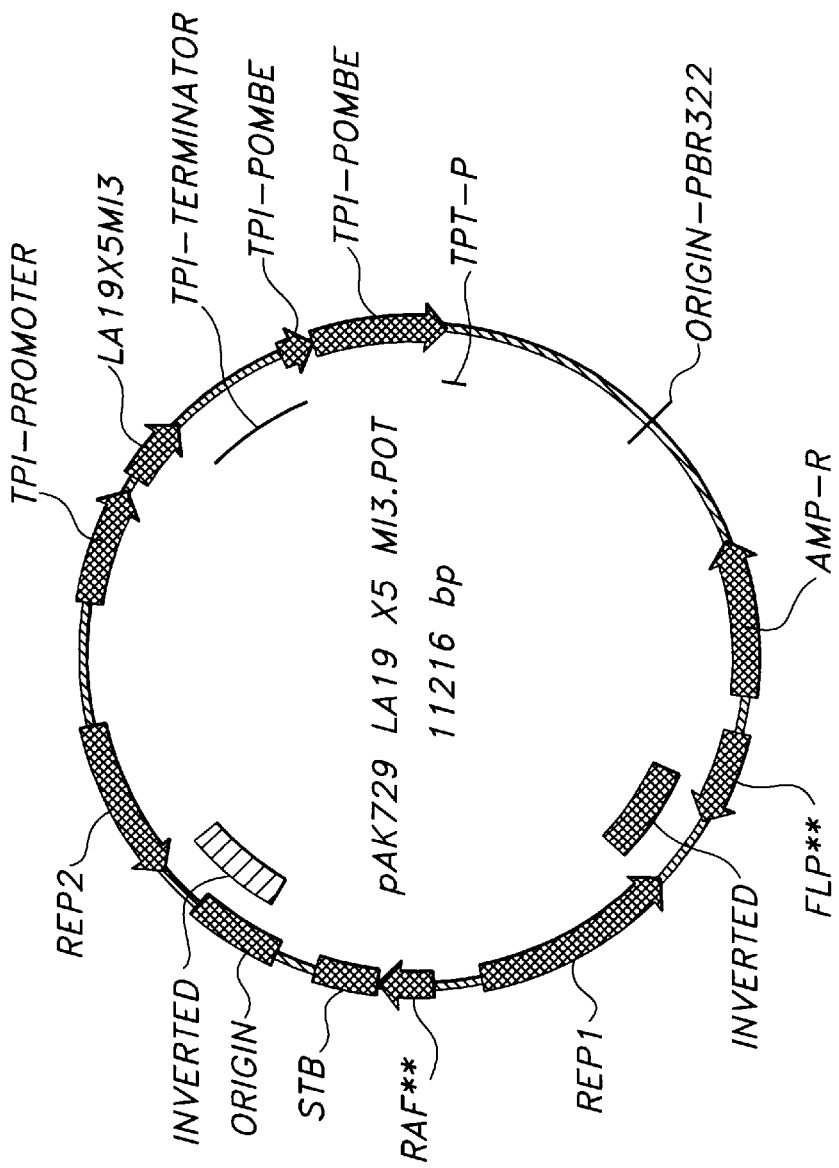
FIG. 1 shows the expression plasmid pAK729 which contains a gene expressing an insulin precursor under expression control of a TPI promoter and a TPI terminator sequence from S. cerevisiae and a signal leader sequence consisting of the YAP3 signal peptide and a synthetic LA19 leader peptide. The construction of pAK729 is described in WO 97/22706. The plasmid also contains the AMP-R sequence from pBR322/pUC13 including the ampicillin resistance gene and an origin of DNA replication in E. coli.

The in vitro deletion of the antibiotic resistance marker gene is done either by use of available restriction sites or by introduction of suitable restriction sites by use of PCR, site specific mutagenesis or other well know techniques for manipulation of DNA sequences followed by treatment with the suitable restriction enzymes.

Four modified NN729 strains were constructed to evaluate whether various deletions in the plasmid might influence the insulin precursor fermentation yield or strain stability during long-term fermentation (Table I). The strains were compared with the original NN729 strain with respect to fermentation yield and fermentation stability (Table II). In addition three modified yeast strain producing a GLP-1 variant Arg$^{34}$GLP-1$_{(7-37)}$ were constructed to evaluate whether various deletions in plasmid pKV228 containing the AMP gene might influence the Arg$^{34}$GLP-1$_{(7-37)}$ fermentation yield (Table III).

Plasmids and strains wherein the AMP gene and possibly surrounding sequences have been deleted are all denoted "ΔAMP".

The modified yeast strains were prepared by transformation of the pAK729 or pKV228 modified plasmids in which the AMP marker gene and possible other DNA sequences from the original plasmid had been deleted into S. cerevisiae strain MT663 (E2-7B XE11-36 a/α, ΔtpiΔtpi,pep 4-3/pep 4-3) or ME1719 (MATa/αΔyap3::ura3/Δyap3::URA3pep4-3/pep4-3Δtpi::LEU2/Δtpi::LEU2 eu2/leu2 Δura3/Δura3).

The modified plasmids were prepared by used of suitable restriction enzyme sites already present in the plasmid or by insertion of suitable restriction enzyme sites in such a way that the AMP gene can be deleted. The modified plasmids can be manipulated in vitro before transformation into S. cerevisiae (strain MT663) in such a way that the AMP gene is deleted or made non-functional and consequently the resulting yeast strain lacks the AMP gene. Thus, potential risk for environmental contamination with the AMP gene during disposal of the yeast cells is eliminated.

The modified pAK729 or pKV228 plasmids were digested with the appropriate restriction enzymes, subjected to agarose electrophoresis, isolated, re-ligated and subsequently transformed into competent MT663 and competent ME1719 WO98/01535 S. cerevisiae cells respectively.

The protein or polypeptide produced by the method of the invention may be any heterologous protein or polypeptide which may advantageously be produced in a yeast cell. Examples of such proteins are aprotinin, tissue factor pathway inhibitor or other protease inhibitors, insulin, insulin precursors or insulin analogues, insulin-like growth factor I or II, human or bovine growth hormone, interleukin, tissue plasminogen activator, transforming growth factor a or b, glucagon, glucagon-like peptide 1 (GLP-1), glucagon-like peptide 2 (GLP-2), GRPP, Factor VII, Factor VIII, Factor XIII, platelet-derived growth factor, and enzymes, such as lipases.

By "a precursor of insulin" or "a precursor of an insulin analogue" is to be understood a single-chain polypeptide, including proinsulin, which by one or more subsequent chemical and/or enzymatic processes can be converted to a two-chain insulin or insulin analogue molecule having the correct establishment of the three disulphide bridges as found in natural human insulin. The insulin precursors will typically contain a modified C-peptide bridging the A- and B chain of insulin. In addition the preferred insulin precursors will lack the B(30) amino acid residue. Most preferred insulin precursors are those described in e.g. EP 163529 and PCT application Nos. 95/00550 and 95/07931. Examples of insulins are human insulin, preferably des(B30) human insulin, and porcine insulin. Preferred insulin analogues are such wherein one or more of the natural amino acid residues, preferably one, two, or three have been substituted by another codable amino acid residue. Thus in position A21 a parent insulin may instead of Asn have an amino acid residue selected from the group comprising Ala, Gln, Glu, Gly, His, Ile, Leu, Met, Ser, Thr, Trp, Tyr or Val, in particular an amino acid residue selected from the group comprising Gly, Ala, Ser, and Thr. Likewise, in position B28 a parent insulin may instead of Pro have an amino acid residue selected from the group comprising Asp, Lys etc., and in position B29 a parent insulin may instead of Lys have the amino acid Pro.

The expression "a codable amino acid residue" as used herein designates an amino acid residue which can be coded for by the genetic code, i. e. a triplet ("codon") of nucleotides.

The DNA constructs used may be prepared synthetically by established standard methods, e.g. the phosphoamidite method described by S. L. Beaucage and M. H. Caruthers, Tetrahedron Letters 22, 1981, pp. 1859–1869, or the method described by Matthes et al., EMBO Journal 3, 1984, pp. 801–805. According to the phosphoamidite method, oligonucleotides are synthesized, e.g. in an automatic DNA synthesizer, purified, duplexed and ligated to form the synthetic DNA construct. A currently preferred way of preparing the DNA construct is by polymerase chain reaction (PCR), e.g. as described in Sambrook et al., Molecular Cloning: A Laboratory Manual, Cold Spring Harbor, N.Y., 1989).

The DNA coding for the desired protein may also be of genomic or cDNA origin, for instance obtained by preparing a genomic or cDNA library and screening for DNA sequences coding for all or part of the polypeptide or the invention by hybridization using synthetic oligonucleotide probes in accordance with standard techniques (cf. Sambrook et al., Molecular Cloning: A Laboratory Manual, Cold Spring Harbor, 1989).

Finally, the DNA encoding the desired protein may be of mixed synthetic and genomic, mixed synthetic and cDNA or mixed genomic and cDNA origin prepared by annealing fragments of synthetic, genomic or cDNA origin (as appropriate), the fragments corresponding to various parts of the entire DNA construct, in accordance with standard techniques.

The recombinant expression vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. The vector system may be a single vector or plasmid or two or more vectors or plasmids which together contain the total DNA to be introduced into the genome of the host cell, or a transposon.

The recombinant expression vector may will contain a DNA sequence encoding the desired protein or polypeptide operably connected to a suitable promoter sequence. The promoter may be any DNA sequence which shows transcriptional activity in yeast and may be derived from genes encoding proteins either homologous or heterologous to yeast. The promoter is preferably derived from a gene encoding a protein homologous to yeast. Examples of suitable promoters are the *Saccharomyces cerevisiae* Mα1, TPI, ADH or PGK promoters.

The DNA sequence encoding the desired protein or polypeptide may also be operably connected to a suitable terminator, e.g. the TPI terminator (cf. T. Alber and G. Kawasaki, *J. Mol. Appl. Genet.* 1, 1982, pp. 419–434).

The recombinant expression vector of the invention will also comprise a DNA sequence enabling the vector to replicate in yeast. Examples of such sequences are the yeast plasmid 2μ replication genes REP 1–3 and origin of replication. The vector may also comprise a selectable marker, e.g. the Schizosaccharomyces pompe TPI gene as described by P. R. Russell, *Gene* 40, 1985, pp. 125–130.

Finally, the expression vector will preferably contain a signal/leader sequence to ensure secretion of the desired protein or polypeptide to the culture medium. A signal sequence is a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The secretory signal sequence may encode any signal peptide which ensures efficient direction of the expressed polypeptide into the secretory pathway of the cell. The signal peptide may be naturally occurring signal peptide, or a functional part thereof, or it may be a synthetic peptide. Useful signal peptides for yeast host cells are obtained from the genes for *Saccharomyces cerevisiae* a-factor and *Saccharomyces cerevisiae* invertase, the signal peptide of mouse salivary amylase (cf. O. Hagenbuchle et al., *Nature* 289 1981, pp. 643–646), a modified carboxypeptidase signal peptide (cf. L. A. Valls et al., *Cell* 48, 1987, pp. 887–897), the yeast BAR1 signal peptide (cf. WO 87/02670), or the yeast aspartic protease 3 (YAP3) signal peptide (cf. M. Egel-Mitani et al., *Yeast* 6, 1990, pp.127–137).

For efficient secretion in yeast, a sequence encoding a leader peptide may also be inserted downstream of the signal sequence and upstream of the DNA sequence encoding the polypeptide. The function of the leader peptide is to allow the expressed polypeptide to be directed from the endoplasmic reticulum to the Golgi apparatus and further to a secretory vesicle for secretion into the culture medium (i.e. exportation of the polypeptide across the cell wall or at least through the cellular membrane into the periplasmic space of the yeast cell). The leader peptide may be the yeast a-factor leader (the use of which is described in e.g. U.S. Pat. No. 4,546,082, EP 16 201, EP 123 294, EP 123 544 and EP 163 529). Alternatively, the leader peptide may be a synthetic leader peptide that is a leader peptide not found in nature. Synthetic leader peptides may be constructed as described in WO 89/02463 or WO 92/11378 and by Kjeldsen et al in "Protein Expression and Purification 9, 331–336 (1997).

The expression "leader peptide" is understood to indicate a peptide in the form of a propeptide sequence whose function is to allow the heterologous protein to be secreted to be directed from the endoplasmatic reticulum to the Golgi apparatus and further to a secretory vesicle for secretion into the medium, (i.e. exportation of the expressed protein or polypeptide across the cellular membrane and cell wall, if present, or at least through the cellular membrane into the periplasmic space of a cell having a cell wall).

The procedures used to ligate the DNA sequences coding for the desired protein or polypeptide, the promoter and the terminator, respectively, and to insert them into suitable yeast vectors containing the information necessary for yeast replication, are well known to persons skilled in the art (cf., for instance, Sambrook et al., op.cit.). It will be understood that the vector may be constructed either by first preparing a DNA construct containing the entire DNA sequence coding for the polypeptide of the invention and subsequently inserting this fragment into a suitable expression vector, or by sequentially inserting DNA fragments containing genetic information for the individual elements (such as the signal, leader or heterologous protein) followed by ligation.

The yeast organism used in the process of the invention may be any suitable yeast organism which, on cultivation, produces satisfactory amounts of the desired protein or polypeptide. Examples of suitable yeast organisms may be strains selected from the yeast species *Saccharomyces cerevisiae, Saccharomyces kluyveri, Schizosaccharomyces pombe, Saccharomyces uvarum, Kluyveromyces lactis, Hansenula polymorpha, Pichia pastoris, Pichia methanolica, Pichia kluyveri, Yarrowia lipolytica,* Candida sp., *Candida utilis, Candida cacaoi,* Geotrichum sp., and *Geotrichum fermentans,* preferably the yeast species *Saccharomyces cerevisiae.*

The transformation of the yeast cells may for instance be effected by protoplast formation followed by transformation in a manner known per se. The medium used to cultivate the cells may be any conventional medium suitable for growing yeast organisms. The secreted heterologous protein, a significant proportion of which will be present in the medium in correctly processed form, may be recovered from the medium by conventional procedures including separating the yeast cells from the medium by centrifugation or filtration, precipitating the proteinaceous components of the supernatant or filtrate by means of a salt, e.g. ammonium sulphate, followed by purification by a variety of chromatographic procedures, e.g. ion exchange chromatography, affinity chromatography, or the like. When the protein is secreted to the periplasmic space, the cells are disrupted enzymatically or mechanically.

The desired protein or polypeptide may be expressed and secreted as an N-terminal extended fusion protein as described in WO 97/22706. The N-terminal extension may then be removed from the recovered protein in vitro by either chemical or enzymatic cleavage as well known in the art. It is preferred to conduct the cleavage by use of an enzyme. Examples of such enzymes are trypsin or *Achromobacter lyticus* protease I.

The present invention is described in further detail in the following examples which are not in any way intended to limit the scope of the invention as claimed.

EXAMPLE 1

Yeast Plasmid pAK729 constructed for expression of an insulin precursor (an N-terminal extended B(1-29)-Ala-Ala-Lys-A(1-21) insulin precursor, see WO 97/22706) contains two ApaLI enzyme restriction sites ApaLI (4477) and ApaLI (5723) (see FIG. 1). These restriction sites are situated on each side of the AMP marker gene. Removal of the 1246 nucleotides between the two ApaLI sites in pAK729 will remove the AMP marker gene and some additional *E. coli* derived plasmid DNA.

The pAK729 plasmid was digested with ApaLI restriction enzyme, subjected to agarose electrophoresis, isolated, re-ligated and subsequently transformed into competent *S. cerevisiae* cells (MT663, see EP B0163529) to give transformed yeast strain NN729.1-ΔAMP. The modified expression plasmid was re-isolated from the yeast strain NN729.1-ΔAMP and DNA sequences were verified after PCR generation followed by subcloning of the DNA region featuring the deletion. Likewise, the DNA sequences encoding the insulin precursor were verified on plasmid DNA re-isolated from yeast strain NN729.1-ΔAMP.

Yeast strain NN729.1-ΔAMP was cultured in YPD medium for at 30° C. for 72 hours. The fermentation yield of the insulin precursor was determined by RP-HPLC.

EXAMPLE 2

Figure 2:
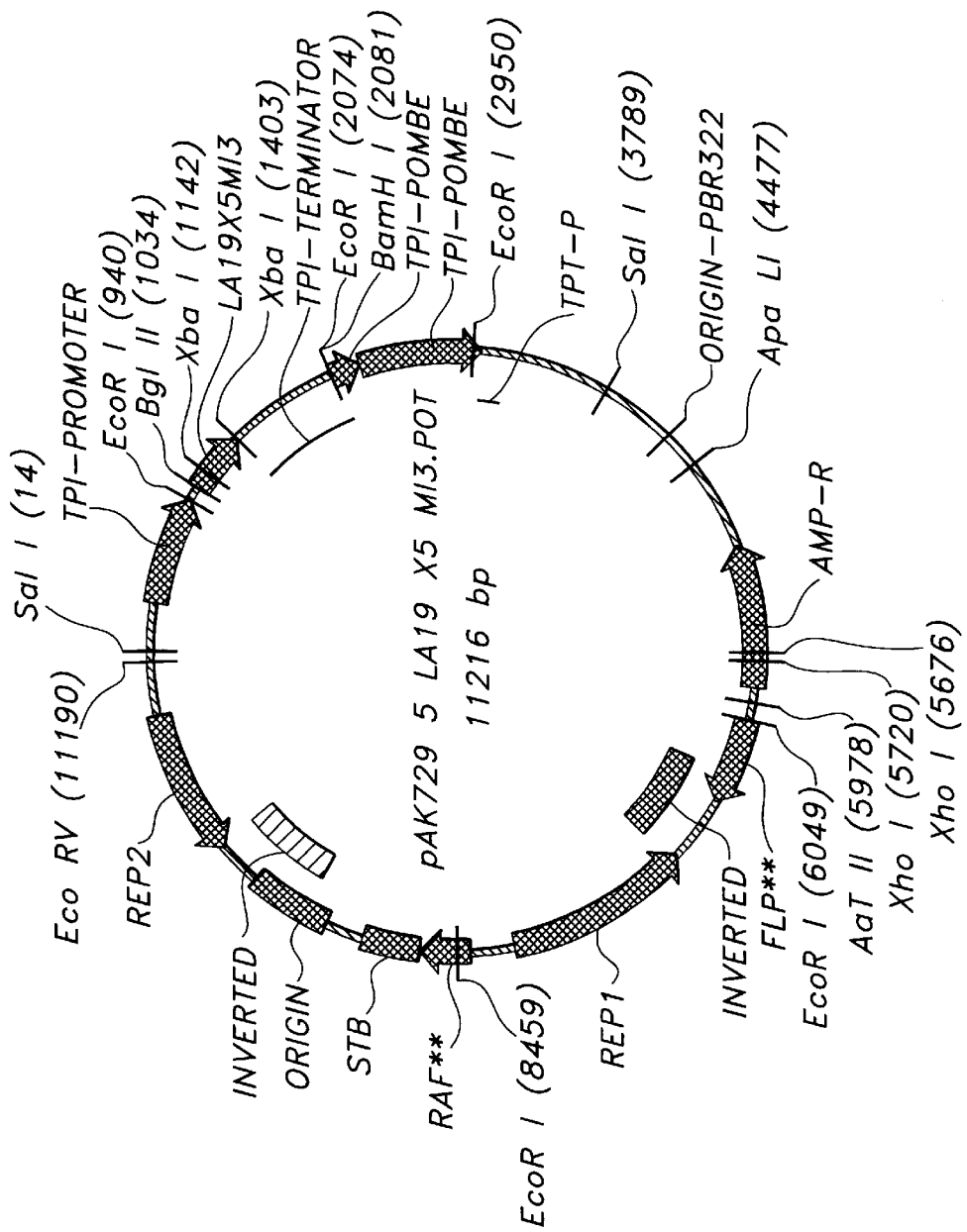
FIG. 2 shows the plasmid map of the pAK729.5 plasmid used for generation of the NN729.5 strain lacking the AMP gene prior to the deletion of the Amp gene.

Enzyme restriction sites, XhoI (5676) and XhoI (5720) were introduced in the pAK729 plasmid by PCR. Selected DNA sequences of the resulting pAK729.5 plasmid were subsequently verified. The restriction plasmid map of pAK729.5 is shown in FIG. 2. The DNA fragment between the restriction enzyme sites XhoI (5676) and XhoI (5720) can be deleted from plasmid pAK729.5 deleting 44 nucleotides localized within the AMP gene.

Plasmid pAK729.5 was digested with XhoI restriction enzymes, subjected to agarose electrophoresis, isolated, re-ligated and subsequently transformed into competent MT663 *S. cerevisiae* cells giving the yeast transformant NN729.5-ΔAMP. The modified expression plasmid was re-isolated from the yeast strain NN729.5-ΔAMP and DNA sequences were verified after PCR generation followed by subcloning of the DNA region featuring the deletion. Likewise, the DNA sequences encoding the insulin precursor were verified on plasmid DNA re-isolated from yeast strain NN729.5-ΔAMP. The 44 nucleotide deletion in pAK729.5-ΔAMP turned out to be as efficient as a complete deletion of the AMP gene with respect to destroying β-lactamase activity.

Yeast strain NN729.5-ΔAMP was cultured in YPD medium for at 30° C. for 72 hours. The fermentation yield of the insulin precursor was determined by RP-HPLC.

EXAMPLE 3

Figure 3:
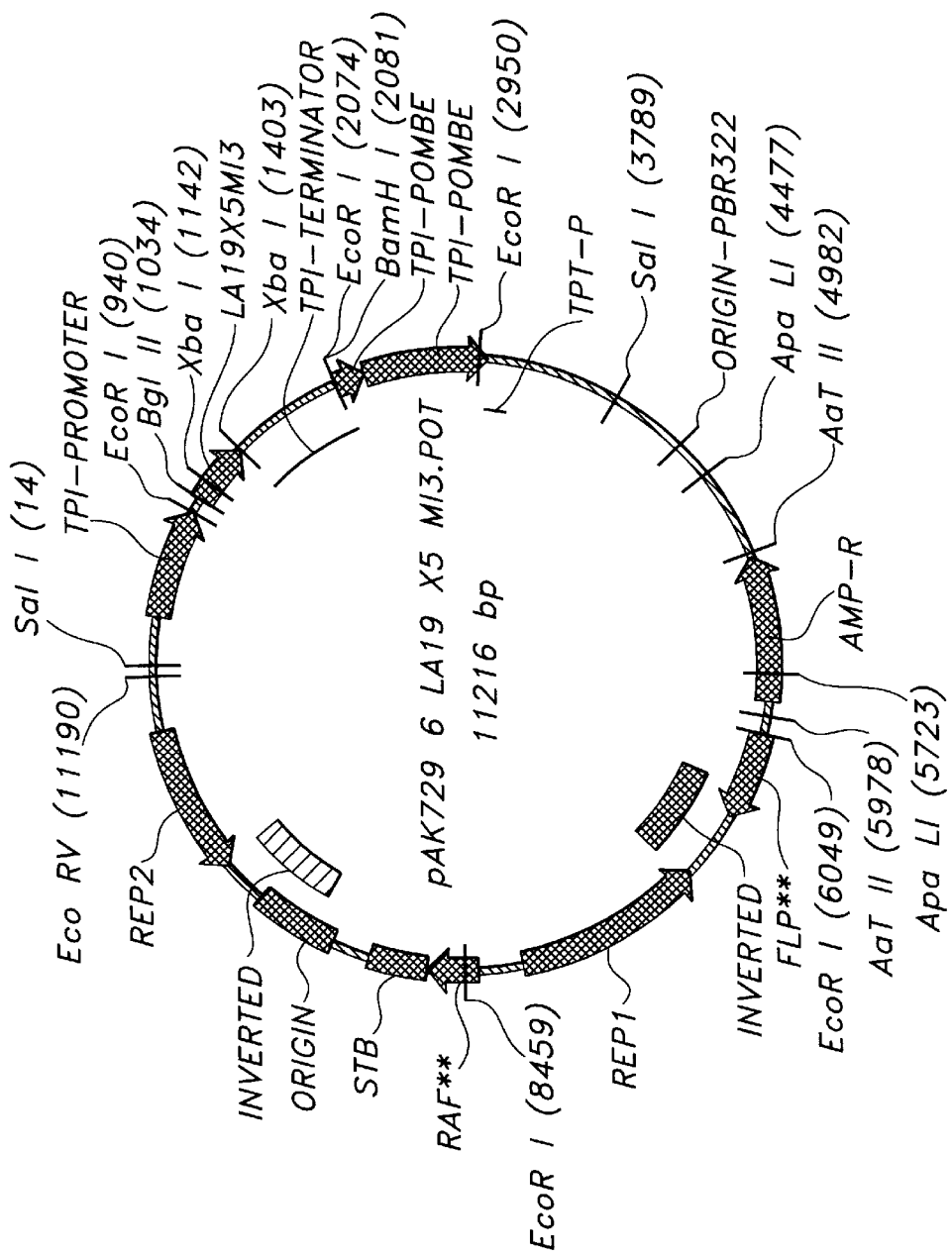
FIG. 3 shows the plasmid map of the pAK729.6 plasmid used for generation of the NN729.6 strain lacking the AMP gene prior to the deletion of the Amp gene.

Enzyme restriction enzyme site, AatlI (4982), was introduced into the the pAK729 plasmid by PCR. Selected DNA sequences of the resulting pAK729.6 plasmid were subsequently verified. The restriction plasmid map of pAK729.6 is shown in FIG. 3. In pAK729.6 the DNA fragment between the restriction enzyme sites Aatll (4982) and Aatll (5978) can be deleted, removing 996 nucleotides from the plasmid. This will remove all of the AMP gene and the promoter.

Figure 4:
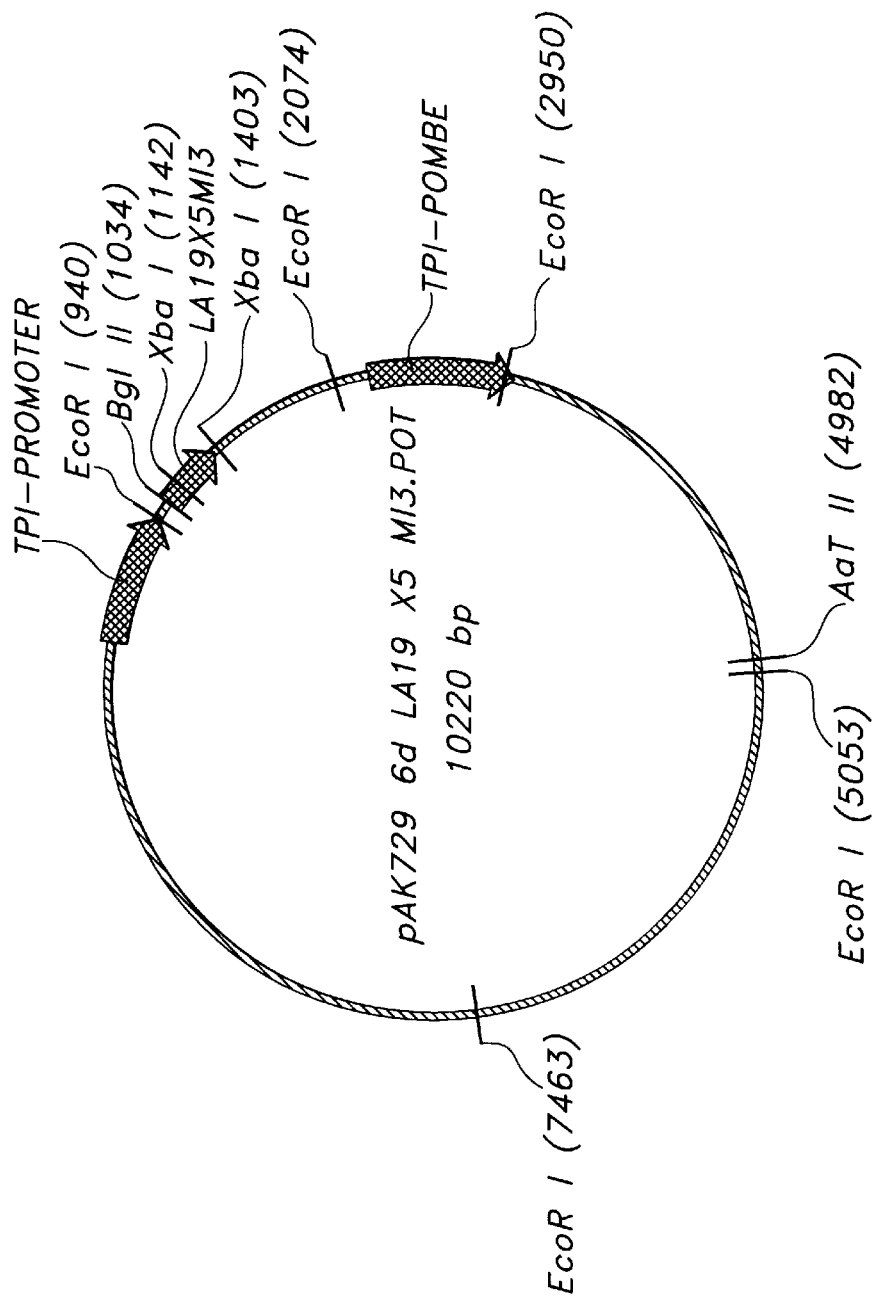
FIG. 4 shows the plasmid map of the pAK729.6-Δamp plasmid in which the AMP gene has been deleted.

The pAK729.6 plasmid was digested with the DNA restriction enzyme AatII, subjected to agarose electrophoresis, isolated, re-ligated and subsequently transformed into competent MT663 *S. cerevisiae* cells. The modified expression plasmid was reisolated from the yeast strain NN729.6-ΔAMP and DNA sequences were verified after PCR generation followed by subeloning of the DNA region featuring the deletion. Likewise, the DNA sequences encoding the insulin precursor were verified on plasmid DNA re-isolated from yeast strain NN729.6-ΔAMP. Plasmid pAK729.6-ΔAMP Lacking the AMP gene is shown in FIG. 4.

Yeast strain NN729.6-ΔAMP was cultured in YPD medium for at 30° C. for 72 hours. The fermentation yield of the insulin precursor was determined by RP-HPLC.

EXAMPLE 4

Figure 5:
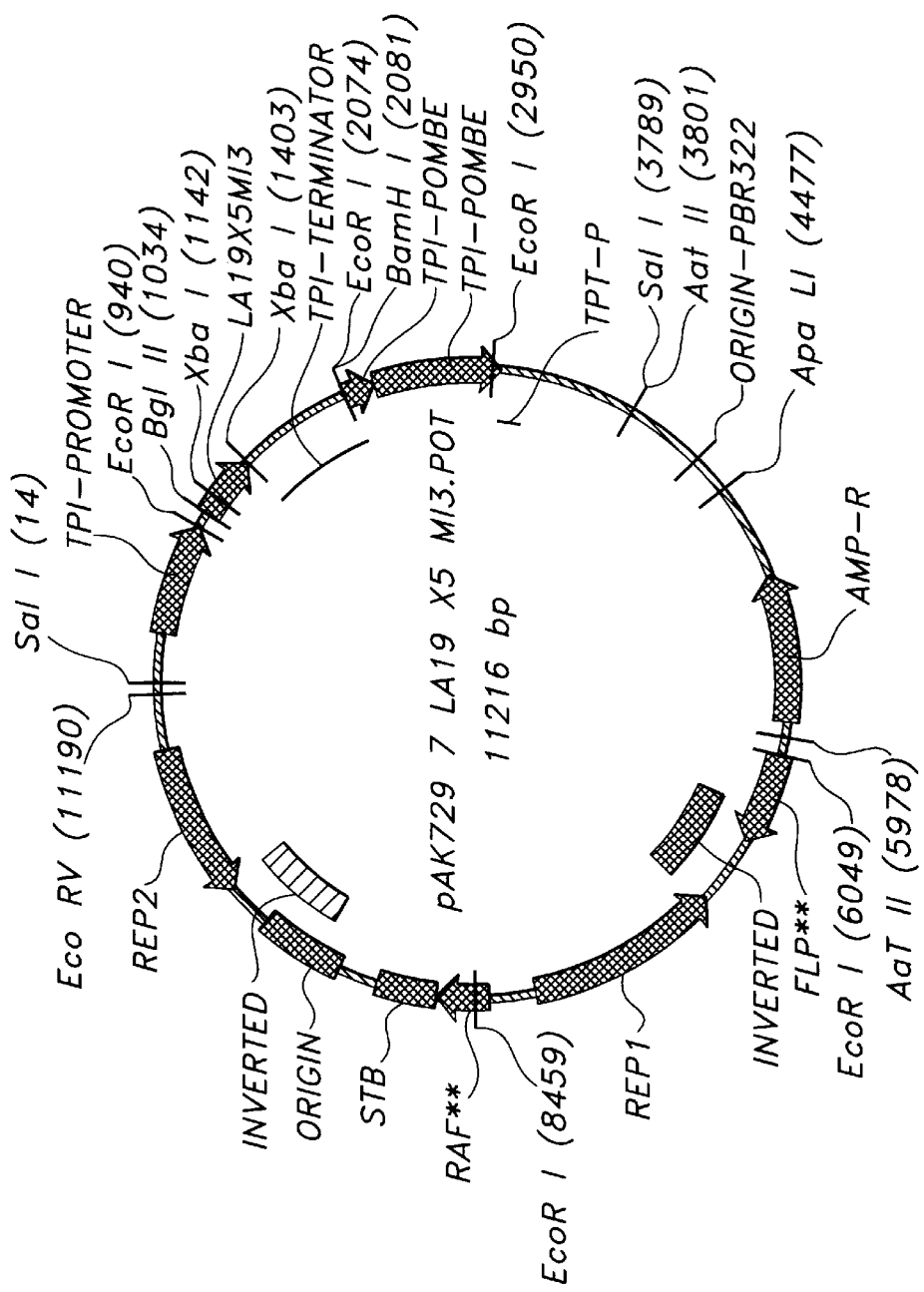
FIG. 5 shows the plasmid map of the pAK729.7 plasmid used for generation of the NN729.7 strain lacking the AMP gene prior to the deletion of the Amp gene.

The new enzyme restriction enzyme site, Aatll (3801), in the pAK729.7 plasmid was introduced into the original pAK729 plasmid by PCR. Selected DNA sequences of pAK729.7 plasmid were subsequently verified. In pAK729.7 the DNA fragment between the restriction enzyme sites Aatll (3801) and Aatll (5978) can be deleted, removing 2177 nucleotides from the expression plasmid. The pAK729.7 plasmid was designed so both the AMP gene and the *E. coli* origin of replication can be deleted. The restriction plasmid map of pAK729.7 is shown in FIG. 5.

The pAK729.7 plasmid was digested with the DNA restriction enzyme AatII, subjected to agarose electrophoresis, isolated, re-ligated and subsequently transformed into competent MT663 *S. cerevisiae* cells. The modified expression plasmid was reisolated from the yeast strain NN729.7-ΔAMP and DNA sequences were verified after PCR generation followed by subcloning of the DNA region featuring the deletion. Likewise, the DNA sequences encoding the insulin precursor were verified on plasmid DNA re-isolated from yeast strain NN729.7-ΔAMP. Yeast strain NN729.7-ΔAMP was cultured in YPD medium for at 30° C. for 72 hours. The fermentation yield of the insulin precursor was determined by RP-HPLC.

TABLE I

Outline of NN729 strains based on pAK729 plasmids with non-functional or deleted AMP gene

| Strain | Plasmid | Modification | Deleted nucleotides |
|---|---|---|---|
| NN729.1-ΔAMP | pAK729.1-ΔAMP | Deletion of sequence between ApaLI (4477) and ApaLI (5723) | 1246 |
| NN729.5-ΔAMP | pAK729.5-ΔAMP | Deletion of the sequence between XhoI$^a$ (5676) and XhoI (5720) | 44 |
| NN729.6-ΔAMP | pAK729.6-ΔAMP | Deletion of the sequence between AatII (5978) and AatII (4982) | 996 |
| NN729.7-ΔAMP | pAK729.7-ΔAMP | Deletion of the sequence between AatII (5978) and AatII (3801) | 2177 |

The new NN729-ΔAMP strains were compared with the original NN729 strain with respect to fermentation yield of the insulin precursor (Table II).

TABLE II

Fermentation yield of NN729 -ΔAMP strains transformed with plasmids with non-functional or deleted AMP gene

| Strain | Yield of the insulin precursor |
|---|---|
| NN729 | 100% |
| NN729.1 | 122% |
| NN729.5 | 110% |
| NN729.6 | 112% |
| NN729.7 | 107% |

It appears from the above that yeast strains comprising an expression plasmid with a partly or fully deleted AMP marker gene express 10–20% more of the insulin precursor compared to the original yeast strain comprising an expression plasmid containing the AMP gene.

EXAMPLE 5

Figure 6:
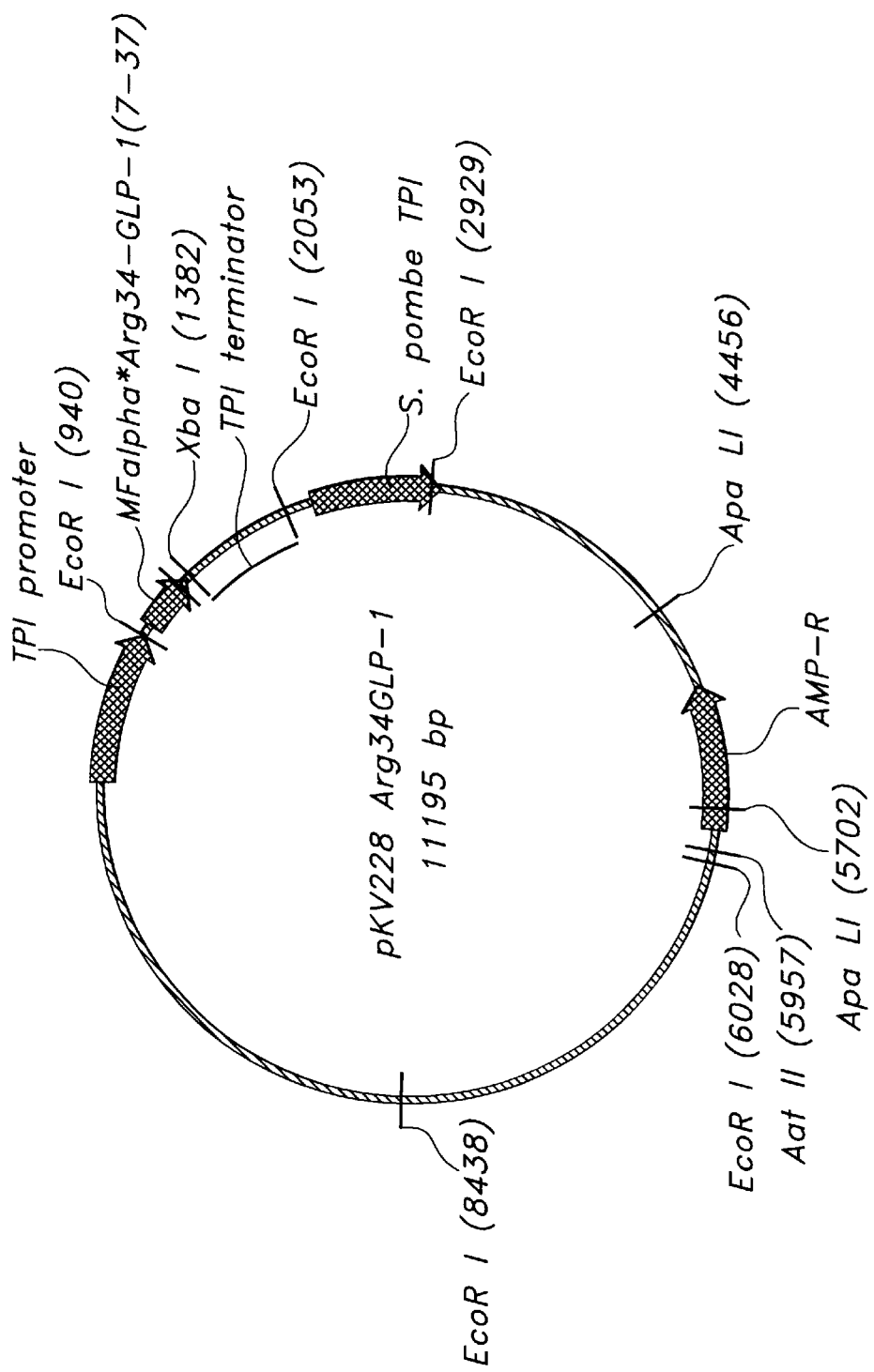
FIG. 6 shows the plasmid map of the pKV228 plasmid modified by replacing the EcoRI (940)-XbaI (1403) coding sequence in pAK729 (FIG. 1) with a MFalpha*-Arg$^{34}$GLP-1$_{(7-37)}$ coding sequence.

Arg$^{34}$GLP-1$_{(7-37)}$ Expression in Yeast Using Plasmids with Non-functional or Deleted AMP Resistance Gene The EcoRI (940)-XbaI (1403) sequence of the pAK729 constructs encoding LA19 X5 MI3 illustrated in FIGS. 1–5 were replaced with an MFalpha*-Arg$^{34}$GLP-1$_{(7-37)}$ coding sequence for the present example (FIG. 6). A modification of the MFα1 pre-pro leader peptide (Kurjan & Herskowitz, Cell 30, 1982. pp. 933.) in which Leu in position 82 and Asp in position 83 have been substituted with Met and Ala respectively introducing the NcoI cleavage site in the DNA sequence was applied in this constructs. The leader sequence was designated MFα1* (Kjeldsen T. et al. 1996). The MFα1 signal MFα1* leader peptide sequence includes the dibasic Kex2p recognition motif (Lys-Arg) separating the leader from the coding sequence for Arg$^{34}$GLP-1$_{(7-37)}$. The peptide Arg$^{34}$GLP-1$_{(7-37)}$ is a human GLP-1$_{(7-37)}$ variant (S. Mojsov, et al., J Biol. Chem. 261, 1986, pp. 11880–11889) wherein the natural amino acid residue in position 34 is substituted with an Arg residue.

Three Arg34GLP-1$_{(7-37)}$ expression plasmids were constructed with AMP resistance gene disruptions as described for NN729.1 (Example 1), NN729.5 (Example 2) and NN729.6 (Example 3) and subsequently transformed into competent ME1719 (see WO098/01535) S. cerevisiae cells giving the yeast transformants YES2076, YES2079 and YES2085, respectively.

The host strain, which was been used to express Arg34GLP-1(7-37), is a diploid strain and has phenotypes which lack two asparatyl proteases, i.e., (1) yeast aspartyl protease 3 (YAP3) which cleaves C-terminal side of mono- or dibasic amino acid residues (Egel-Mitani, et al., YEAST 6: 127–137, 1990) and (2) vacuolar protease A responsible for activation of other proteases such as protease B, carboxypeptidase Y, aminopeptidase I, RNase, alkaline phosphatase, acid trehalase and exopolyphosphatase. Moreover the triose phosphate isomerase gene (TPI) has been disrupted, which phenotype makes it possible to utilize glucose in transformants grown on glucose containing medium. The genetic background of ME1719 is MATa/a Dyap3::ura3/Dyap3::URA3 pep4-3/pep4-3 tpi::LEU2/Dtpi::LEU2 leu2/leu2 Dura3/Dura3.

The modified expression plasmids pKV301, pKV307 and pKV304 were re-isolated from the yeast strains and DNA sequences were verified after PCR generation followed by subcloning of the DNA region featuring the deletion. Likewise, the DNA sequences encoding Arg$^{34}$GLP-1$_{(7-37)}$ was verified on plasmid DNA re-isolated from the yeast strains. Table III shows a comparison between modified and non-modified strains.

TABLE III

Outline of YES strains based on plasmids with non-functional or deleted AMP resistance gene for expression of Arg$^{34}$GLP-1$_{(7-37)}$

| Strain | Plasmid | Modification | Deleted nucleotides | Comparison of Arg$^{34}$GLP-1$_{(7-37)}$ yields |
|---|---|---|---|---|
| YES1757 | pKV228 | Non | 0 | 100% |
| YES2076 | pKV301 | Deletion of sequence between ApaLI (4456) and ApaLI (5702) | 1246 | 119% |
| YES2079 | pKV307 | Deletion of sequence between XhoI (5655) and XhoI (5699) | 44 | 113% |
| YES2085 | pKV304 | Deletion of sequence between AatII (5957) and AatII (4961) | 996 | 136% |

Yields were compared from 5 ml laboratory scale fermentations in YPD for 72 hours at 30° C. Yields were evaluated using HPLC.

What is claimed is:

1. A method for preparing a yeast strain stably transformed with an extrachromosomal yeast expression plasmid, said method comprising:

(I) providing an isolated first yeast expression plasmid comprising a functional antibiotic resistance marker gene;

(ii) modifying the antibiotic resistance marker gene in vitro to produce a second yeast expression plasmid, wherein the second plasmid either (a) contains an inactivated antibiotic resistance marker gene or (b) lacks the antibiotic marker gene present on the first plasmid; and (iii) introducing the second plasmid into a recipient yeast cell to produce said yeast strain transformed with the second plasmid.

2. A method as defined in claim 1, wherein said extrachromosomal yeast expression plasmid comprises a DNA sequence encoding a polypeptide of interest.

3. A method as defined in claim 1, wherein the in vitro modification comprises subjecting the first plasmid to digestion with one or more restriction enzymes, wherein said one or more restriction enzymes recognize sequences within or flanking said antibiotic resistance marker gene.

4. A method for producing a polypeptide of interest, said method comprising culturing transformed yeast cells produced using a method as defined in claim 1 under conditions in which said polypeptide is expressed by said cells.

5. A method as defined in claim 4, wherein the expressed polypeptide is secreted into the culture medium of said cells.

6. A method as defined in claim 4, wherein the expressed polypeptide is an insulin precursor or an insulin analogue precursor.

7. A method as defined in claim 4, wherein the expressed polypeptide is a GLP-1 precursor.

* * * * *